United States Patent
Lo

(10) Patent No.: US 6,190,411 B1
(45) Date of Patent: Feb. 20, 2001

(54) FIXING ELEMENT AND LIGAMENT FIXED WITH FIXING ELEMENT

(76) Inventor: Kokbing Lo, Sportlaan 28, 7576 WV Oldenzaal (NL)

(*) Notice: Under 35 U.S.C. 154(b), the term of this patent shall be extended for 0 days.

(21) Appl. No.: 09/155,677

(22) PCT Filed: Apr. 1, 1997

(86) PCT No.: PCT/NL97/00162

§ 371 Date: Jan. 29, 1999

§ 102(e) Date: Jan. 29, 1999

(87) PCT Pub. No.: WO97/36557

PCT Pub. Date: Oct. 9, 1997

(30) Foreign Application Priority Data

Apr. 2, 1996 (NL) .................................................... 1002753
Feb. 27, 1997 (NL) .................................................... 1005394

(51) Int. Cl.⁷ .................................................... A61F 2/08
(52) U.S. Cl. .................................... 623/13.13; 623/13.14
(58) Field of Search ................................ 623/16, 17, 13, 623/13.11, 13.12, 13.13, 13.14

(56) References Cited

U.S. PATENT DOCUMENTS

| | | | |
|---|---|---|---|
| 4,744,793 | * | 5/1988 | Parr et al. ........................ 623/13.13 |
| 4,828,562 | * | 5/1989 | Kenna ............................. 623/13.13 |
| 4,870,957 | * | 10/1989 | Goble et al. . |
| 5,002,574 | * | 3/1991 | May et al. . |
| 5,263,984 | | 11/1993 | Li et al. .............................. 623/15 |
| 5,507,812 | | 4/1996 | Moore ................................ 623/13 |

FOREIGN PATENT DOCUMENTS

| | | |
|---|---|---|
| 8701123 | 4/1987 | (DE) . |
| 3710587 | 10/1988 | (DE) . |
| 2663837 | 1/1992 | (FR) . |

* cited by examiner

Primary Examiner—David J. Isabella
(74) Attorney, Agent, or Firm—Webb Ziesenheim Logsdon Orkin & Hanson, P.C.

(57) ABSTRACT

Disclosed is a fixing element for connecting a ligament to a bone part of a human or animal. The fixing element includes a hollow, substantially cylindrical element fixable in a continuous opening in the bone part, and an engaging element for the ligament anchorable in the cylindrical element at least at two mutually differing axial positions.

11 Claims, 3 Drawing Sheets

FIXING ELEMENT AND LIGAMENT FIXED WITH FIXING ELEMENT

The invention relates to a fixing element for connecting a ligament to a bone part of a human or animal, comprising:
- a hollow, substantially cylindrical element fixable in the continuous opening in the bone part, and
- an engaging element for the ligament anchorable in the cylindrical element at least at two mutually differing axial positions.

When a ligament is damaged, for instance a hamstring is torn (ligament rupture) it is possible to arrange a new ligament surgically (plastic ligament). For such a new ligament can be used ligament material removed from another location in the body, but plastic material (plastic ligament) can also be employed for this purpose. The fixing of the ligament can take place for instance by means of a screw with toothed ring, staples, a bone plug, a toothed plug and so on. Fixing by means of a bone plug entails a continuous opening being arranged in a bone part through which the ligament for fixing is placed, The bone segment coming from the bone part and used for making the continuous opening is subsequently placed in the ligament such that the ligament is clamped fixedly in the continuous opening by the bone segment or bone plug. All these fixing methods are frequently used singly or in combination.

Drawbacks of the existing fixing method are that it is difficult to bring the ligament to, and hold it at, the correct tension. The consequence hereof is reduced function, pain and a sensation of instability. A drawback which applies particularly to a ligament manufactured from a ligament material removed from another location in the body (homologous) is that a ligament operatively arranged at the correct tension can slacken in the course of time whereby instability once again increases. A drawback to plastic ligament material is that this has a finite life-span so that it generally breaks after a number of years. The ligament will then have to be replaced and this is only possible by means of another major operation.

FR-A-2 663 837 describes a fixing element for connecting a ligament to a bone part. The fixing element comprises a hollow cylindrical element, which is fixable in a continous opening in the bone part and an engaging element for anchoring the ligament in the cylindrical element. The engaging element comprises a screw for displacing the engaging element in the cylindrical element.

The object of the present invention is to fix a ligament to a bone part such that it is very simple to hold the ligament to or vary tension respectively to replace a fixed ligament with another.

The present invention provides for this purpose a fixing element which is characterized in that the inner wall of the cylindrical element is provided with a profile for co-action with and axial positioning of the engaging element for the ligament.

See further page 2, line 14: "The outer wall ..." placed and this is only possible by means of another major operation.

The object of the present invention is to fix a ligament to a bone part such that it is very simple to hold the ligament to or vary tension respectively to replace a fixed ligament with another.

The present invention provides for this purpose a fixing element for connecting a ligament to a bone part of a human or animal, comprising:
- a hollow, substantially cylindrical element fixable in the continuous opening in the bone part, and
- an engaging element for the ligament anchorable in the cylindrical element at least at two mutually differing axial positions. The outer wall of the cylindrical element is preferably provided with a profile for a stable anchoring thereof in the bone part. The cylindrical element forms the engaging option for the engaging element which is connected to the ligament. The engaging element is connectable in relatively simple manner to the cylindrical element whereby displacement of the engaging element relative to the cylindrical element is comparatively simple to realize or whereby it in possible to release an engaging element with ligament fixed thereto from the cylindrical element and to replace it with a new ligament likewise provided with an engaging element, irrespective of the ligament type. It will be apparent that it is of great importance herein that the cylindrical element be rigidly connected to the bone part. The operative technique to be used does not differ greatly from the usual technique. For a simple connection between the cylindrical element and the engaging element the inner wall of the cylindrical element is preferably provided with a profile for co-action with the engaging element for the ligament. This internal profile can more preferably be formed by internal screw thread. For a simple and good coupling of the engaging element to the cylindrical element the outer side of the engaging element is preferably also provided with a profile for co-action with the inner side of the cylindrical element. This profile is preferably also formed by a screw thread. Readjustment of the ligament tension can take place for instance using a limited surgical operation such as for instance with an incision under local anaesthetic. In a preferred embodiment it is possible to provide the fixing element with adjusting means controllable from a distance. Herein can be envisaged for instance micromotors or induction principles. The tension on the ligament can then be adjusted "in the field" using a remote control or on a production line or while the patient is connected up to a knee laxity measuring apparatus. Other solutions are also conceivable in this respect, such as for instance temperature-sensitive materials or adjusting means controllable by means of a moving magnetic field.

Owing to the construction with the hollow cylindrical element which is permanently anchorable in the bone, the actions required for a possible revision are very limited and the revision time can be markedly reduced compared with the revision time for an existing ligament anchoring. The revision can be performed arthroscopically.

On at least one side of the cylindrical element the inner side preferably transposes smoothly into the end wall of the cylindrical element. When the cylindrical element is placed in the bone part such that the smooth transition of the inner side into the end wall forms the side along which the ligament is carried into the cylindrical element, excessive wear of the ligament resulting from contact with a sharp edge can be prevented.

The engaging element is preferably provided with means for clamping the ligament. Clamping of the ligament has the advantage that the ligament material is hereby not damaged, or hardly so, and that the ligament length required for a particular operation remains as limited as possible. The engaging element can be used irrespective of the type of implant (homologous, plastic ligament or combination).

In a preferred embodiment the engaging element comprises a continuous opening in which a clamping element is anchorable for clamping the ligament. Such a clamping construction is very reliable and moreover simple in use.

In another preferred embodiment the engaging element is connectable to the cylindrical element with interposing of a resilient element. By means of such a resilient connection the ligament tension can be held constant despite for instance stretching of the ligament material occurring in the course of time. Another advantage is that peak loads on the ligament can be at least partially absorbed by the resilient element, whereby damage to a ligament will occur less quickly.

In yet another preferred embodiment the engaging element is provided on the side remote from the ligament with at least one recess and/or projecting part for engagement of adjusting means for altering the position of the engaging element relative to the cylindrical element. By means of this provision it becomes possible to vary the tension on the ligament post-operatively using a very small incision. By inserting an adjusting means, for instance in the form of a spanner, into the incision such that it co-acts with the recess and/or projecting part it becomes possible to alter the position of the engaging element relative to the cylindrical element. A major surgical operation is therefore no longer necessary to change the tension on the ligament.

The invention also relates to a ligament fixed with at least one fixing element to a bone part. It is possible to anchor the ligament on two sides with the fixing elements according to the invention but a significant advantage can already be achieved when one side of the ligament is fixed with the fixing elements according to the invention while the other side can be fixed according to a method of the prior art.

BRIEF DESCRIPTION OF THE DRAWINGS

The present invention will be further elucidated with reference to the non-limitative embodiments shown in the following figures. Herein.

DETAILED DESCRIPTION OF THE PREFERRED EMBODIMENTS

Figure 1:
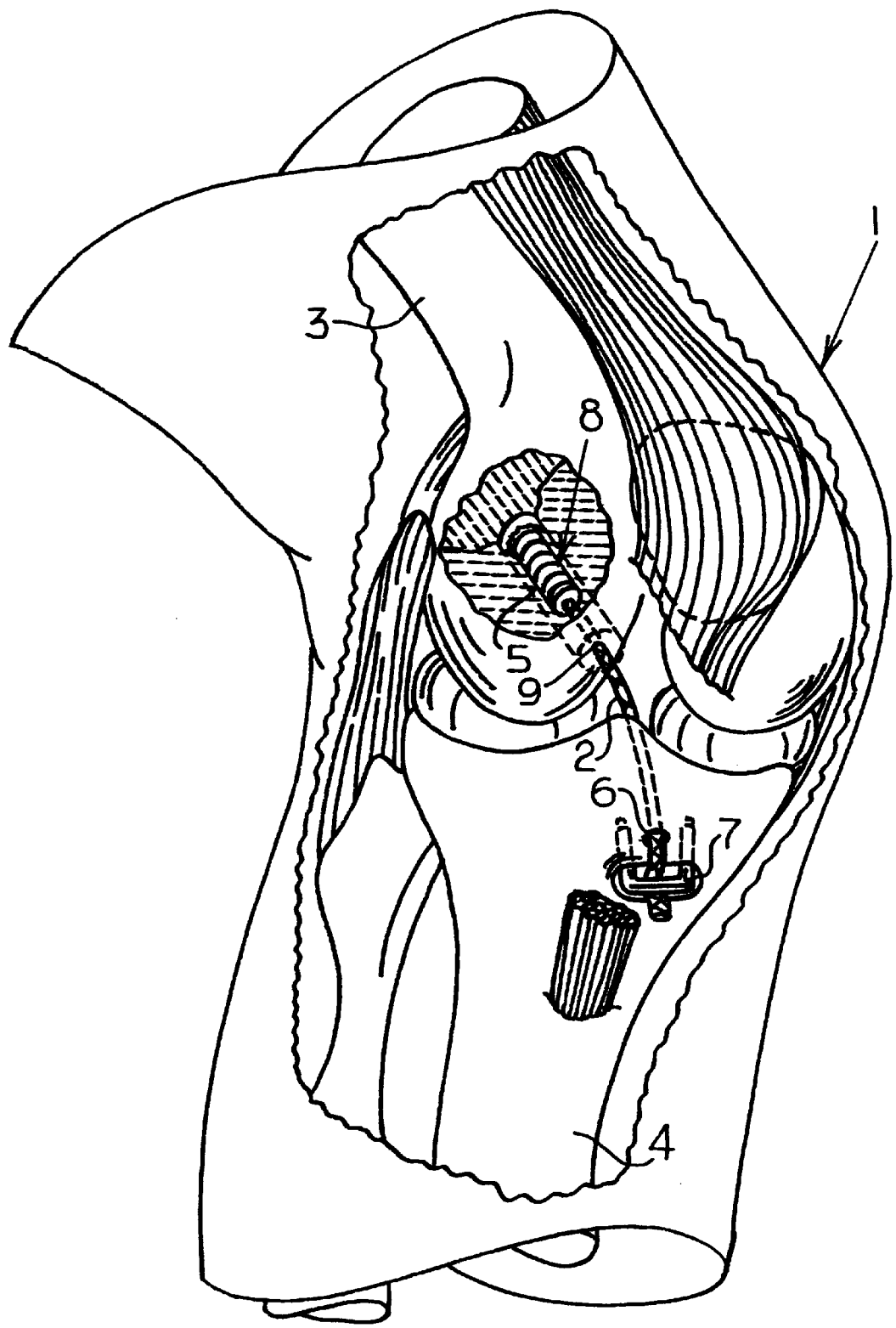
FIG. 1 shows a cut away perspective view of a knee provided with a ligament fixed on one side with a fixing element according to the invention.

FIG. 1 shown a knee joint 1 of a human body which is partly cut away. A ligament 2 is fixed artificially in knee joint 1. Arranged for this purpose in both an upper bone part 3 and a lower bone part 4 are respective continuous openings 5, 6. Ligament 2 is fixed to lower bone part 4 by means of a staple 7 known in the prior art. Such a connection of ligament 2 to lower bone part 4 provides a rigid connection which can only be released by way of a surgical operation. It is also difficult herein to fix the same staple 7 for a second time at the same position on lower bone part 4.

In upper bone part 3 a fixing element 8 according to the invention is arranged in the continuous opening 5. The side of the fixing element facing toward ligament 2 is provided with an edge 9 rounded on the inside to prevent wear of ligament 2 where it enters fixing element 8. Reference is made to the following figures for a further elucidation of fixing element 8.

Figure 2:
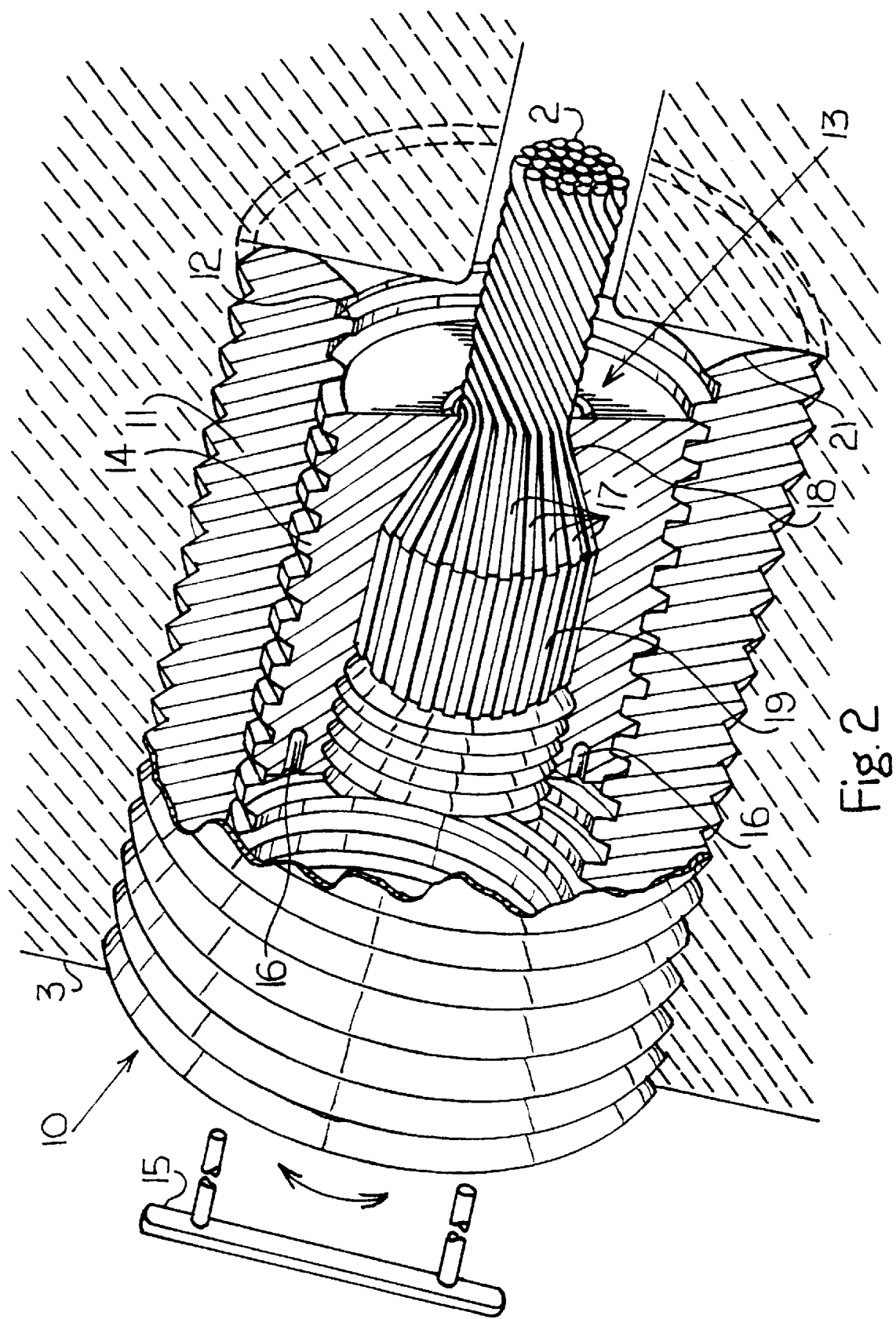
FIG. 2 is a perspective view of a fixing element according to the invention.

FIG. 2 shows a fixing element 10 received in a bone part 3. Fixing element 10 comprises a cylindrical element 11, the outer side of which is provided with a profiled edge for a stable fixing of cylindrical element 11 in the bode material 3. Cylindrical element 11 takes at hollow form such that the inner wall is provided with an internal screw thread 12.

Situated in cylindrical element 11 is an engaging element 13 provided with an external screw thread 14, which screw thread 14 co-acts with internal screw thread 12 of cylindrical element 11. By rotating engaging element 13 relative to cylindrical element 11 the former will be displaced in axial direction. This axial displacement of engaging element 13 will change the tension on the ligament 2. By placing for instance a spanner 15 in recesses 16 arranged in the end wall of engaging element 13 the tension on the ligament 2 can be varied in very simple manner. Ligament 2 as shown in these figures is constructed from a large number of fibres 17. Other ligaments are however also conceivable. For fixing of engaging element 13 to ligament 2 the engaging element 13 is provided with a recess 18 in which a clamping element 19 is situated. Clamping element 19 can be anchored in recesses 18 such that the fibres 17 of ligament 2 are clamped between clamping element 13 and the wall of the recess. In this figure the clamping element is provided for this purpose with a screw thread which co-acts with an internal screw thread arranged over a part of the length of recess 18. Other solutions can however also be envisaged herefor.

Figure 3:
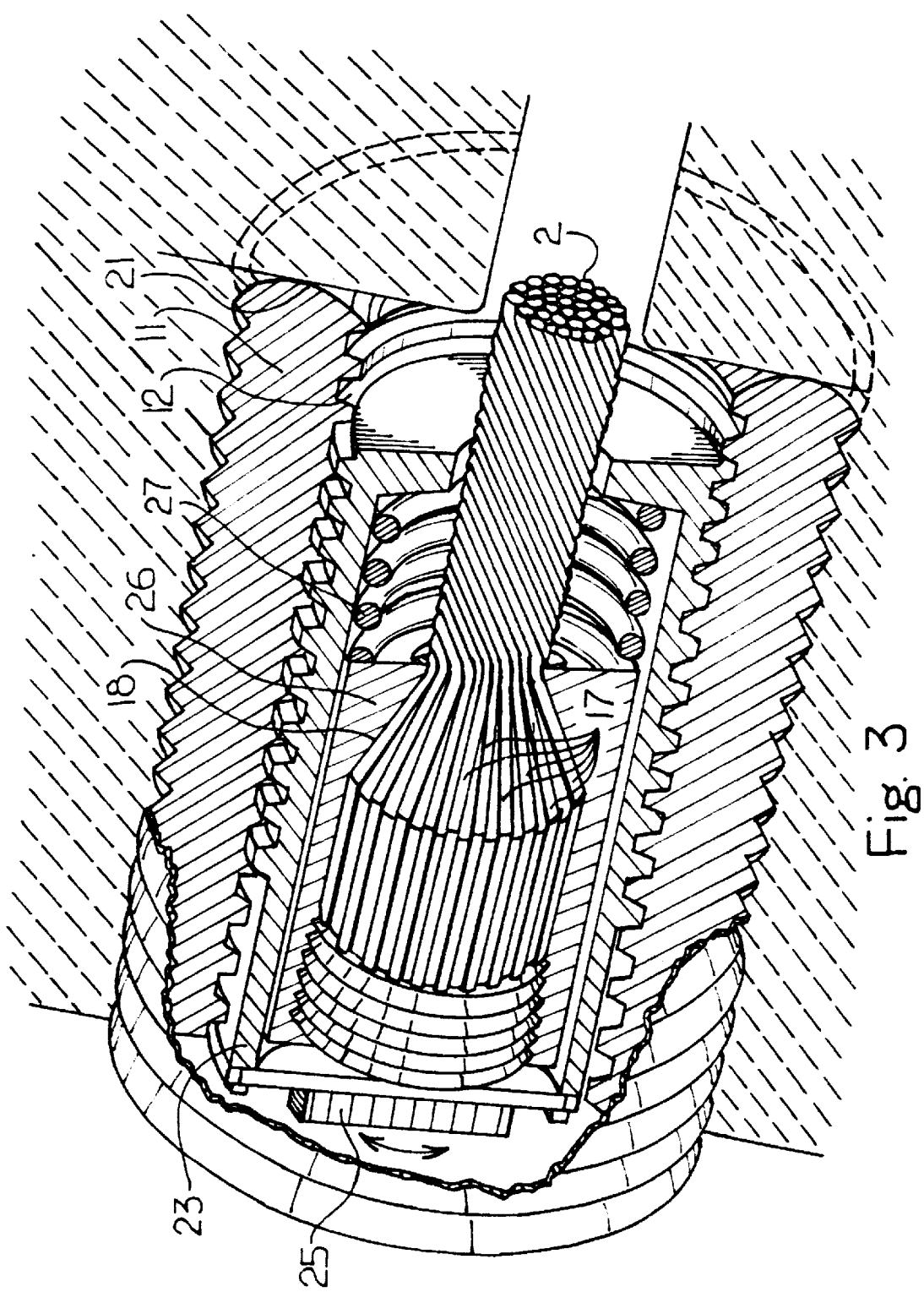
FIG. 3 is a perspective view of another fixing element according to the invention.

FIG. 3 shows a fixing element 20 with a construction which differs from the fixing element 10 shown in FIG. 2. The fixing element 20 shown here likewise comprises a cylindrical element 11 which corresponds with the element shown in FIG. 2. On the side where ligament 2 can come into contact with cylindrical element 11 the latter is provided with a rounded edge 21. Situated in cylindrical element 11 is an engaging element 22 with a hollow jacket 23, this latter being provided with an external screw thread 24 for co-action with internal screw thread 12 of cylindrical element 11. By rotating fixing element 20, which is simplified by a protrusion 25 mounted on jacket 23, the position of the jacket 23 can be varied in an axial direction relative to cylindrical element 11. At variance with the construction as shown in FIG. 2, a clamping block 26 greatly resembling clamping element 19 as shown in FIG. 2 is received for free axial movement in jacket 23. The operation of the clamping block will not be further elucidated in these figures. Clamping block 26 supports by means of a spring 27 on jacket 23. The tension on ligament 2 will hereby remain constant in the case of small changes in the length of ligament 2; the changes in length of ligament 2 can be absorbed by the spring 27. The fixing element 20 shown in this figure therefore has the advantage that in the case of small changes in the length of the ligament 2 readjustment do not have to be carried out in order to retain a constant tension on ligament 2.

What is claimed is:

1. A fixing element for connecting a ligament to a human or animal bone part, comprising:

a hollow, substantially cylindrical element fixable in a continuous opening through the bone part and extending substantially a full length of the opening; and a cylindrical engaging element for the ligament, the engaging element positioned axially within the cylindrical element wherein an inner wall of the cylindrical element is provided with a profile for co-action with a profiled outer wall of the engaging element such that the engaging element is displaceable axially relative to the cylindrical element for changing tension of the ligament.

2. The fixing element as claimed in claim 1, wherein the profile of the inner wall of the cylindrical element is formed by an internal screw thread.

3. The fixing element as claimed in claim 1, wherein an outer wall of the cylindrical element is provided with a profile for anchoring the cylindrical element in the bone part.

4. The fixing element as claimed in claim 1, wherein the fixing element is provided with adjusting means for axially displacing the engaging element relative to the cylindrical element and changing the tension of the ligament.

5. The fixing element as claimed in claim 1, wherein at least one end face of the cylindrical element transposes smoothly into the inner wall of the cylindrical element.

6. The fixing element as claimed in claim 1, wherein the engaging element is provided with means for clamping the ligament.

7. The fixing element as claimed in claim 1, wherein the profiled outer wall of the engaging element is formed by a screw thread.

8. The fixing element as claimed in claim 1, wherein the engaging element includes a continuous opening in which a clamping element is anchorable for clamping the ligament.

9. The fixing element as claimed in claim 1, wherein the engaging element is connectable to the cylindrical element with the interposing of a resilient element.

10. The fixing element as claimed in claim 1, wherein the engaging element is provided on a side remote from the ligament with at least one recess for engagement of adjusting means for changing the axial position of the engaging element relative to the cylindrical element.

11. The fixing element as claimed in claim 1, wherein the engaging element is provided on a side remote from the ligament with at least one projecting part for engagement of adjusting means for changing the axial position of the engaging element relative to the cylindrical element.

* * * * *

UNITED STATES PATENT AND TRADEMARK OFFICE
CERTIFICATE OF CORRECTION

PATENT NO. : 6,190,411 B1  
DATED : February 20, 2001  
INVENTOR(S) : Kokbing Lo Page 1 of 1

It is certified that error appears in the above-identified patent and that said Letters Patent is hereby corrected as shown below:

Title Page,
Item [30], Foreign Application Priority Data, "Apr. 2, 1996" should read -- Apr. 1, 1996 --.

Column 1,
After Title, insert -- BACKGROUND OF THE INVENTION --.
Delete text from line 55 that begins "See further" and continuing through to Column 2, line 1, ending with "axial positions."

Column 2,
Line 6, "in relatively" should read -- in a relatively --.
Line 9, "it in" should read -- it is --.
Line 10, "with ligament" should read -- with a ligament --.
Line 21, after "formed by" insert -- an --.

Column 3,
Line 65, "bode material" should read -- bone material --.
Line 66, "takes at hollow" should read -- takes a hollow --.

Signed and Sealed this

Fifteenth Day of January, 2002

Attest:

JAMES E. ROGAN
*Director of the United States Patent and Trademark Office*

*Attesting Officer*